United States Patent [19]

Monte

[11] Patent Number: 5,603,936
[45] Date of Patent: Feb. 18, 1997

[54] PROCESS FOR REMOVING LIGHT ABSORBING COMPOUNDS FROM EPIDERMAL PLANT CELLS

[75] Inventor: Woodrow C. Monte, Tempe, Ariz.

[73] Assignee: Richard A. Ratcliff, Scottsdale, Ariz.; a part interest

[21] Appl. No.: 389,023

[22] Filed: Feb. 15, 1995

[51] Int. Cl.⁶ .......................... A61K 35/78; A61K 38/46; A61K 38/47; A61K 38/48

[52] U.S. Cl. .................. 424/195.1; 424/94.6; 424/94.61; 424/94.62; 424/94.63; 424/94.64; 424/94.65; 424/94.66; 514/456

[58] Field of Search ................................ 424/94.6–94.66, 424/195.1; 514/456

[56] References Cited

U.S. PATENT DOCUMENTS 5,202,122   4/1993   Graves et al. ........................ 424/195.1

Primary Examiner—John W. Rollins
Attorney, Agent, or Firm—Tod R. Nissle

[57] ABSTRACT

A process is provided for harvesting light absorbing compounds from the epidermal cells of a plant. The plant is subjected to artificial light having wavelengths in the range of 260 to 400 nm. The plant is ground to form a slurry and an enzyme is added to the slurry to breach the walls of cells in the plant to free the light absorbing compounds. A solvent added to the slurry extracts the light absorbing chemicals.

20 Claims, No Drawings

PROCESS FOR REMOVING LIGHT ABSORBING COMPOUNDS FROM EPIDERMAL PLANT CELLS

This invention relates to a process for harvesting light absorbing compounds from the epidermal cells of a plant.

In a further respect, the invention relates to a liquid food composition including light absorbing compounds stored in the epidermal cells of a plant.

In another respect, the invention relates to a topical ointment or gel which protects the skin from sunlight and which includes light absorbing compounds manufactured by a plant.

Sulphoraphane, PEITC (phenethylisothiocyanate), indole-3-carbinol, aurones, chalcones, anthocyanidins, flavanones, anthocyanidins, flavones, flavonols, flavan 3-ols, oligomeric flavonoids, biflavonoids, isoflavonoids and other compounds stored in the epidermal cells of plants typically absorb light having wavelengths in the range 10 to 800 nm. The harvesting and use of such light absorbing compounds outside of a plant has apparently been limited or non-existent.

In accordance with the invention, I have discovered a process for concentrating, harvesting, and utilizing such compounds. In accordance with one aspect of the invention, I provide a process for harvesting plant compounds which are stored in the epidermis of a plant and which absorb light having a wavelength in the range of 280 to 380 nm. The process includes the initial step of subjecting at least a portion of a plant for a selected period of time to artificial light comprising light having wavelengths in the range of 260 nm to 400 nm and a selected illuminance of greater than 3000 lumens per square foot. After the plant has been subjecting to this artificial light, it is ground to form a slurry including epidermal cells from the plant. An enzyme is mixed in the slurry to produce an enzyme reaction slurry. The enzyme promotes the breaching of the outer walls of cells to release the plant compounds from the epidermal cells. The presently preferred enzyme is cellulase, although alpha amylase, lypase, and protease can also be utilized, as can other protein hydrolyzing enzymes, starch dextrinizing enzymes, starch saccharifying enzymes, and cellulose hydrolyzing enzymes. A solvent is added to the enzyme reaction slurry to form a solvent-enzyme reaction slurry. The solvent extracts the plant compounds from said enzyme reaction slurry. The solvent is separated from the solvent-enzyme reaction slurry. The solvent can then, if desired, be evaporated to separate the plant compounds from the solvent. Solvents such as DMSO, ethanol, liquid carbon dioxide, and methanol are presently preferred.

In another embodiment of the invention, I provide a liquid food composition for ingestion by a human being. The food composition includes from 40.0 % to 98.0% by weight water; from 1.0% to 50% by weight powder; and, from 0.001% to 1.0% by weight of a plant compound which is stored in the epidermal cells of a plant and which in the plant absorbs light having at least one wavelength in the range of 260 to 400 nm. The powder includes from 4% to 22% by weight of triglycerides of predominantly 6 to 26 carbon atoms in the fatty acid chains; from 6% to 28% by weight of water soluble protein alpha-amino acids; from 56% to 75% by weight of carbohydrates selected from the group consisting of corn syrup solids, trisaccharide, tetrasaccharides, pentasaccharides, hexasaccharides, dextrose, fructose, maltose, logsaccharides and high saccharides; from 0.1% to 6.0% by weight of an emulsifier; and, from 0.1% to 6.0% by weight of an edible acid for adjusting the pH of the food composition within the range of 2.0 to 6.5.

In a further embodiment of the invention, I provide a drink for ingestion by a human being. The drink comprises from 50.0% to 99.999% by weight water; and, from 0.001% to 1.0% by weight of a plant compound which is stored in the epidermal cells of a plant and which in the plant absorbs light having a wavelength in the range of 260 to 400 nm.

In still another embodiment of the invention, I provide a process for protecting the epidermis of a human being from sunlight. The process comprises applying to the epidermis a composition including a carrier; and, at least one plant compound which is stored in the epidermis of a plant and which in the plant absorbs light having a wavelength in the range of 260 to 400 nm.

The following examples depict the presently preferred embodiments of the invention for the purpose of illustrating the practice thereof and not by way of limitation of the scope of the invention. In the examples, all proportions are by weight, unless otherwise noted.

EXAMPLE 1

Ten grams of a four hundred gram sample of epidermal tissue from freshly picked rhubarb leaves grown out-of-doors is, after the leaves are all carefully washed with warm water, tested to determine the total concentration of aurones in the leaves. The leaves are free from insect damages, and are not bruised. The remaining three hundred and ninety gram portion of the sample is subjected to artificial light including a spectrum of light waves having wavelengths of from 260 to 400 nm (nanometers) for twenty-four consecutive hours at an intensity of 1000 lumens per square foot. Twenty grams of the three hundred and ninety gram portion of the sample is then tested for the total concentration of the aurones in the leaves. The total concentration in weight of aurones per gram of leaves in the twenty gram sample increases by over two hundred percent in comparison to the concentration of the same compound in the leaves before the leaves are subjected to the 260 to 400 nm light for twenty-four hours.

EXAMPLE 2

Example 1 is repeated, except that the ten gram and twenty gram samples are each tested for the concentration of anthocyanidins instead of for the concentration of aurones. The concentration of anthocyanidins is greater in the twenty gram sample than in the ten gram sample. The period of time during which the sample is subjected to the 260 to 400 nm light can vary as desired. Increasing the length of time appears to increase the concentration of the aurones in the plant.

EXAMPLE 3

Ten grams of a four hundred gram sample of freshly cut broccoli grown out-of-doors is, after the broccoli is carefully washed in warm water, tested to determine the concentration of sulphoraphane, PEITC (phenethylisothiocyanate), and indole-3-carbinol in the broccoli. The broccoli is ripe and is free from insect and other damage. The remaining three hundred and ninety gram portion of the sample is subjected at room temperature to artificial light including a spectrum of light waves having wavelengths of from 260 to 400 nm (nanometers) for twenty-four consecutive hours at an intensity of 500 lumens per square foot. Twenty grams of the three hundred and ninety gram portion of the sample is then tested for the concentration of sulphoraphane, PEITC, and indole-3-carbinol. The concentration in weight of sulphoraphane, PEITC, and indole-3-carbinol per gram of broccoli of the twenty gram sample increases by over one hundred percent in comparison to the concentration of sulphoraphane, PEITC, and indole-3-carbinol in the freshly cut broccoli before the broccoli was subjected to the 260 to 400 nm light for twenty-four hours.

EXAMPLE 4

One hundred grams of the 390 gram portion of the sample subjected to artificial sunlight in Example 3 is ground to one hundred mesh and is contacted with five grams of cellulase enzyme for three hours to form an extraction mixture. The cellulase enzyme promotes the breaching of cell walls to release sulphoraphane, PEITC (phenethylisothiocyanate), and indole-3-carbinol in the broccoli.

EXAMPLE 5

Twenty five grams of the extraction mixture of Example 4 is mixed for an hour with twenty-five grams of DMSO-d6 to extract the sulphoraphane, PEITC, and indole-3-carbinol into the DMSO. After the hour has elapsed, the DMSO-d6 is separated from the extraction mixture. The DMSO-d6 carries sulphoraphane, PEITC, and indole-3-carbinol.

EXAMPLE 6

Twenty five grams of the extraction mixture of Example 4 is mixed with twenty-five grams of ethanol at room temperature for one hour to extract sulphoraphane, PEITC, and indole-3-carbinol from the extraction mixture into the ethanol. After the hour has elapsed, the ethanol is separated from the extraction mixture. The ethanol carries sulphoraphane, PEITC, and indole-3-carbinol.

EXAMPLE 7

Examples 4 to 6 are repeated except that in Example 4 five grams of beta amylase enzyme is substituted for the five grams of cellulase enzyme. Similar results are obtained. The amylase enzyme promotes breakdown of cellular walls.

EXAMPLE 8

Example 4 to 6 are repeated except that in Example 4 five grams of lipase enzyme is substituted for the five grams of cellulase enzyme. Similar results are obtained. The lipase enzyme promotes breakdown of cellular walls.

EXAMPLE 9

Examples 4 to 6 are repeated except that in Example 4 five grams of protease enzyme is substituted for the five grams of cellulase enzyme. Similar results are obtained. The protease enzyme promotes breakdown of cellular walls.

EXAMPLE 10

Examples 3 to 6 are repeated, except that broccoli purchased from the produce department of a Smith's supermarket in Phoenix, Arizona is substituted for the fresh cut broccoli. The broccoli is standard store broccoli, has not dried, consists in large part of living broccoli cells, is maintained in a cooled produce area, and is intermittently sprayed with water by store personnel. The store broccoli is ripe and is free from insect and other damage. Similar results are obtained in each of Examples 3 to 6.

EXAMPLE 11

Ten grams of a four hundred gram sample of epidermal tissue from freshly picked Thompson Seedless grapes grown out-of-doors is, after the grapes are all carefully washed with warm water, tested to determine the total concentration of chemical compounds including aurones, chalcones, anthocyanidins, flavanones, anthocyanidins, flavones, flavonols, flavan 3,4-diols, oligomeric flavonoids, biflavonoids, and isoflavonoids in the epidermal tissue. The grapes are ripe and juicy, are free from insect damages, and are not bruised. The remaining three hundred and ninety gram portion of the sample is subjected to artificial light including a wavelength of 302 nm (nanometer) for one hour at an intensity of one lumen per square foot. Twenty grams of the three hundred and ninety gram portion of the sample is then tested for the total concentration of the aurones, chalcones, anthocyanidins, flavanones, anthocyanidins, flavones, flavonols, flavan 3-ols, oligomeric flavonoids, biflavonoids, and isoflavonoids in the grape. The total concentration in weight of aurones, chalcones, anthocyanidins, flavanones, anthocyanidins, flavones, flavonols, flavan 3-ols, oligomeric flavonoids, biflavonoids, and isoflavonoids per gram of grapes in the twenty gram sample increases by over one hundred percent in comparison to the concentration of the same compounds in the grapes before the grapes were subjected to the 302 nm light for one hours. The length of time during which the sample is exposed to the 302 nm light can vary as desired. Increasing the length of time appears to increase the concentration of the aurones, chalcones, etc. in the sample.

EXAMPLE 12

One hundred grams of the 390 gram portion of the sample of grapes in Example 11 which was subjected to the 302 nm light is ground to one mesh and is contacted with five grams of cellulase enzyme for three hours at room temperature to form an extraction mixture.

EXAMPLE 13

Twenty-five grams of the extraction mixture of Example 12 is mixed for an hour at room temperature with twenty five grams of DMSO-d6 to extract aurones, chalcones, anthocyanidins, flavanones, flavones, flavonols, flavan 3,4-diols, oligomeric flavonoids, biflavonoids, and isoflavonoids into the DMSO. After the hour has elapsed, the DMSO-d6 is separated from the extraction mixture. The DMSO-d6 carries aurones, chalcones, anthocyanidins, flavanones, anthocyanidins, flavones, flavonols, flavan 3,4-diols, oligomeric flavonoids, biflavonoids, and isoflavonoids.

EXAMPLE 14

Twenty-five grams of the extraction mixture of Example 12 is mixed with twenty five grams of ethanol at room temperature for one hour to extract aurones, chalcones, anthocyanidins, flavanones, flavones, flavonols, flavan 3,4-diols, oligomeric flavonoids, biflavonoids, and isoflavonoids from the extraction mixture into the ethanol. After the hour has elapsed, the ethanol is separated from the extraction mixture. The ethanol carries aurones, chalcones, anthocyanidins, flavanones, anthocyanidins, flavones, flavonols, flavan 3-ols, oligomeric flavonoids, biflavonoids, and isoflavonoids.

EXAMPLE 15

Examples 11 to 14 are repeated except that the artificial light used in Example 11 has a spectrum of wavelengths in the range of 400 to 800 nm and an illuminance of 20,000 lumens per square foot. Similar results are obtained.

EXAMPLE 16

Examples 11 to 14 are repeated except that the light used in Example 11 has an intensity of 100 lumens per square foot. Similar results are obtained.

EXAMPLE 17

Examples 11 to 14 are repeated except that the light used in Example 11 has an intensity of five lumens per square foot. Similar results are obtained. In the practice of the invention, one or more wavelengths of artificial light can be utilized to illuminate one or more parts of a plant in order to increase the concentration of a light absorbing compound in the plant. The illuminance of the light can be adjusted as desired, as can the time the plant is exposed to the light. In some cases, it might be desirable to expose a plant to a single wavelength of light in the range of 260 to 800 nm for a minute or less at a small illuminance of one lumen per square foot. This could be the case when it is desired to increase the concentration in a plant of one or more particular light absorbing compounds. In another case, it might be desirable to expose a plant to artificial light containing a spectrum of wavelengths in the range of 260 to 800 nm and at a high illuminance greater than 10,000 lumens per square foot for twenty-four hours or more. The wavelength, illuminance, and length of time the plant is exposed to the artificial light preferably, but not necessarily, are selected to that the plant is not burned or otherwise damaged.

EXAMPLE 18

Examples 11 to 17 are repeated except that in Example 11 400 grams of epidermal tissue from freshly picked apricots are carefully washed with warm water and substituted for the 400 grams of grapes. The apricots are ripe and juicy, are not bruised, and are free from insect damage. Similar results are obtained.

EXAMPLE 19

Examples 11 to 17 are repeated except that in Example 11 400 grams of freshly picked carrots are carefully washed with warm water and are substituted for the 400 grams of grape epidermal tissue. The carrots are ripe, are free from insect and other damage. Similar results are obtained.

EXAMPLE 20

Example 18 is repeated except that epidermal tissue from apricots purchased from the produce department of a Smith's supermarket in Phoenix, Arizona are carefully washed with warm water and are substituted for the freshly picked apricots. The apricots are standard store apricots, are ripe and juicy, have not been dried, consist in large part of living apricot cells, and were maintained in a cooled produce area in the store. Similar results are obtained.

EXAMPLE 21

Pea leaf tendrils grown in continuous light including light having a spectrum of wavelengths of from 400 to 800 nm were tested to determine the total topographic distribution (the "Total Quantity") in umoles per g fr wt of the group of chemical compounds including aurones, chalcones, anthocyanidins, flavanones, flavones, flavonols, flavan 3,4-diols, oligomeric flavonoids, biflavonoids, and isoflavonoids. The results are shown below in TABLE I. Each sample noted in TABLE I was extracted from about ten milligrams of tendril tissue.

TABLE I

| Part of Tendril | Total Quantity umoles per g fr wt |
| --- | --- |
| Apical fourth | 7.21 + 0.07 |
| Second fourth | 5.62 + 0.81 |
| Third fourth | 3.10 + 0.20 |
| Basal fourth | 1.86 + 0.07 |

EXAMPLE 22

The uptake of C-sucrose, fructose, glucose, maltose and ribose in buds on the stems of pea plants and the plumule growth was evaluated when the plants were subjected at room temperature for twenty-four hours to light having a wavelength of 6500 angstroms and light having a wavelength of 7000 angstroms. One sample of pea plant buds was exposed to the 6500 angstrom light while another sample was exposed to the 7000 angstrom light. Exposure to the 6500 angstrom light increased the uptake of C-sucrose, fructose, glucose, maltose, and ribose in the buds and increased the plumule growth. Exposure to the 7000 angstrom light did not significantly increase the uptake of C-sucrose, fructose, glucose, maltose, and ribose.

EXAMPLE 23

Examples 11 to 17 are repeated except that in Example 11 400 grams of freshly picked rhubarb leaves are carefully washed with warm water and are substituted for the 400 grams of grapes. The leaves are free from insect and other damage. Similar results are obtained.

EXAMPLE 24

Two hundred ml of boiling water were mixed in a beaker with 13.5 grams of CARBOPOL 940. During the mixing the bottom of the beaker was positioned over and in contact with a reservoir of boiling water. The water-CARBOPOL 940 was mixed for about ten minutes until a smooth gel was formed. The beaker was removed from above the boiling water reservoir and the gel was permitted to cool, was covered with plastic wrap, and was permitted to sit for twenty-four hours so that the CARBOPOL would hydrate.

After the gel sat for twenty-four hours, one hundred ml of PEG 400 and 83 ml of ethyl alcohol SDA40B were mixed for about ten minutes with the gel to form a smooth gel mixture. After the smooth gel mixture was formed, another 600 ml of ethyl alcohol SDA40B were mixed for about ten minutes with the gel to form a smooth gel mixture. After the smooth gel mixture was formed, another 600 ml of ethyl alcohol SDA40B was mixed into the gel mixture and the gel mixture stirred until the additional alcohol had been uniformly dispersed in the gel.

0.3 ml of blue food coloring was stirred into the gel.

3.3 ml triethanolamine was added to 12 ml ethyl alcohol SDA40B. This mixture was then added to the gel to cross link the water to the CARBOPOL and stiffen the gel.

The separated ethanol from Example 14 is mixed into the gel. The Ph of the gel is about 6.7.

The concentration of plant compounds (of the type extracted by ethanol in Example 14) in the gel can vary as desired, but ordinarily the quantity of plant compounds in the gel comprises 0.001% to 1.0% by weight.

EXAMPLE 26

A gel is made in accordance with the process described in EXAMPLE 25, except that 100 grams of a gelatin is utilized in place of the PEG 400 and CARBOPOL 940 and 600 ml of water is substituted for the 600 ml of ethyl alcohol.

EXAMPLE 27

The gel of Example 25 is applied to epidermis of an individual in a thin layer about one thirty second of an inch thick, or less. The gel absorbs 260 nm to 400 nm light. The gel can be applied to the skin in any desired thickness.

EXAMPLE 28

The gel of Example 26 is applied to the epidermis of an individual in a thin layer about one thirty-second of an inch thick, or less. The gel absorbs 260 nm to 400 nm light. The gel can be applied to the skin in any desired thickness.

EXAMPLE 29

A topical ointment is prepared. 1000 grams of white petrolatum q. s. and 200 grams of wool fat are melted and 250 grams of liquid petrolatum (heavy) is added thereto. After the mixture has cooled to at least 40 degrees Centigrade, the separated ethanol from Example 14 is added. The mixture is stirred until the ointment congeals. The concentration of plant compounds (of the type extracted by ethanol in Example 14) in the ointment can vary as desired, but ordinarily the quantity of plant compounds in the ointment comprises 0.001% to 1.0% by weight.

EXAMPLE 30

A topical ointment is prepared. 1000 grams of white petrolatum q. s. and 200 grams of wool fat are melted and 250 grams of liquid petrolatum (heavy) is added thereto. After the mixture has cooled to at least 40 degrees Centigrade, the separated DMSO from Example 13 is added. The mixture is stirred until the ointment congeals. The concentration of plant compounds (of the type extracted by DMSO in Example 13) in the ointment can vary as desired, but ordinarily the quantity of plant compounds in the ointment comprises 0.001% to 1.0% by weight.

EXAMPLE 31

The ointment of Example 29 is applied to epidermis of an individual in a thin layer about one thirty second of an inch thick, or less. The gel absorbs light having wavelengths in the range of 260 nm to 400 nm. The gel can be applied to the skin in any desired thickness.

EXAMPLE 32

The ointment of Example 30 is applied to the epidermis of an individual in a thin layer about one thirty-second of an inch thick, or less. The gel absorbs light having wavelengths in the range of 260 nm to 400 nm. The gel can be applied to the skin in any desired thickness.

EXAMPLE 33

A food composition in powder form is prepared by blending the following ingredients.

| Ingredient | Weight Percent |
| --- | --- |
| MALTODEXTRIN (POLYSACCHARIDES) | 31.00000 |
| MALTODEXTRIN AGGLOMERATED | 24.00000 |
| MCT OIL | 6.70000 |
| CORN OIL | 6.70000 |
| WHEY PROTEIN POWDER | 9.30000 |
| HYDROLYZED PROTEIN POWDER (dipeptides, tripeptides, oligopeptides) | 9.58103 |
| SODIUM ACETATE | 0.88000 |
| POTASSIUM CITRATE | 0.57000 |
| CALCIUM PHOSPHATE | 0.70000 |
| DIPOTASSIUM PHOSPHATE | 0.80000 |
| MAGNESIUM CHLORIDE 6H | 0.90000 |
| FERROUS SULFATE | 0.01400 |
| ZINC SULFATE 1H | 0.01800 |
| MANGANESE SULFATE 1H | 0.00460 |
| CUPRIC SULFATE 5H | 0.00230 |
| CHROMIC CHLORIDE | 0.00012 |
| POTASSIUM IODIDE | 0.00005 |
| SELENIUM OXIDE | 0.00003 |
| MOLYBDENUM TRIOXIDE | 0.00003 |
| LECITHIN | 0.44000 |
| SODIUM ASCORBATE | 0.44000 |
| CHLORINE CHLORIDE | 0.21000 |
| VITAMIN E (500 IU/GM) | 0.05000 |
| NIACINAMIDE | 0.01800 |
| CALCIUM PANTOTHENATE | 0.01600 |
| THIAMINE HYDROCHLORIDE | 0.00250 |
| PYRIDOXINE HYDROCHLORIDE | 0.00300 |
| RIBOFIAVIN | 0.00180 |
| VITAMIN A (250,000 IU/GM) | 0.01000 |
| FOLIC ACID | 0.00044 |
| BIOTIN (1% 10 MG/GM) | 0.02500 |
| VITAMIN K 1% | 0.00430 |
| VITAMIN D3 (1,000,000 IU/GM) | 0.00300 |
| CYANOCOBALAMIN (0.1%) | 0.00580 |
| SOY POLYSACCHARIDE (FIBER) | 7.60000 |
| Total Weight | 100.000000 |

The approximate percent calories from the various ingredients are carbohydrates 52.4%, fat 30.5%, and protein 17.1%. The carbohydrates included in the powder food composition include sucrose, dextrose, maltose, lactose, trisaccharide, tetrasaccharides, pentasaccharides, hexasaccharides, and higher saccharides. When 25 gm of the food powder composition is reconstituted with 75 gm of water the resulting mixture has a caloric density (Cal/ml) of 1.07; a total Cal/Nitrogen ratio of 145.9; a non-protein ratio of 120.9; a protein concentration of 45.8 g/liter; a fat concentration of 36.1 g/liter; a carbohydrate (digestible) concentration of 140 g/liter; a carbohydrate (total) concentration of 153.8 g/liter; and a dietary fiber concentration of 14 g/liter.

During the blending of the above-listed ingredients of the food composition, agglomeration techniques are preferably employed to make the resulting powder mixture more easily dispersed and soluble in water.

EXAMPLE 34

One thousand grams of the food composition powder of Example 33 are mixed with three thousand grams of water and with the separated ethanol from Example 14. The resulting drink provides 1.1 calories per cubic centimeter, has a pH of 4.7, has an osmolarity of 300, has a viscosity of about 90 to 100 centipoise, and has particles each having a size of less than about 100 mesh. The concentration of plant compounds (of the type extracted by ethanol in Example 14) in the resulting drink can vary as desired, but ordinarily the quantity of plant compounds in the resulting drink comprises 0.001% to 1.0% by weight of the resulting drink.

EXAMPLE 35

One thousand grams of a food composition in powder form is prepared by blending the following ingredients in the proportions noted.

| INGREDIENT | WEIGHT PERCENT Dry |
|---|---|
| SUGAR | 5.70 |
| WHEY PROTEIN CONCENTRATE | 15.09 |
| FORETEIN 35 (protein alpha-amino acids) | |
| CALCIUM LACTATE, PENTAHYDRATE | 3.67 |
| CREATIVE CREAMER 829 (fat emulsifier) | 5.70 |
| MALTODEXTRIN, M100 (agglomerated) | 67.23 |
| HERCULES CELLULOSE GUM, CMC-7HF | 1.99 |
| EMULSIFIER, BEATREME 3581Z (fat emulsifier) | .22 |
| VITAMIN PREMIX 110584 (Vitamins A, D, C, K, etc.) | .22 |
| MAGNESIUM OXIDE | .18 |
| TOTAL | 100.00 |

The approximate percent calories from the various ingredients are carbohydrates 50%, fat 30%, and protein 18%. The carbohydrates included in the powder food composition include sucrose, dextrose, maltose, lactose, trisaccharide, tetrasaccharides, pentasaccharides, hexasaccharides, and higher saccharides. When 25 gm of the food powder composition is reconstituted with 75 gm of water the resulting mixture has a caloric density (Cal/ml) of 1; a total Cal/Nitrogen ratio of 140; a non-protein ratio of 120; a protein concentration of 45 g/liter; a fat concentration of 36 g/liter; a carbohydrate (digestible) concentration of 140 g/liter; a carbohydrate (total) concentration of 150 g/liter; and a dietary fiber concentration of 14 g/liter.

EXAMPLE 36

948 grams of food composition powder of EXAMPLE 35 are mixed with 3328 milliliters of water and with the separated ethanol from Example 14. The resulting drink provides about 1 calorie per cubic centimeter, has a pH of about 4.6, has an osmolarity of about 300, has a viscosity of about 90 to 100 centipoise, and has particulate each having a size of less than about 100 mesh. The concentration of plant compounds (of the type extracted by ethanol in Example 14) in the resulting drink can vary as desired, but ordinarily the quantity of plant compounds in the resulting drink comprises 0.001% to 1.0% by weight of the resulting drink.

EXAMPLE 37

The separated ethanol from Example 14 is mixed with 500 ml of water to form a drink. Sweetener, vitamin C, and other desired components can, if desired, be added to the drink. The concentration of plant compounds (of the type extracted by ethanol in Example 14) in the resulting drink can vary as desired, but ordinarily the quantity of plant compounds in the resulting drink comprises 0.001% to 1.0% by weight of the resulting drink.

A plant includes roots, stems, leaves, and buds, as well as the flowers, fruit, and seeds produced by the plant.

Having described my invention in such terms as to enable those skilled in the art to understand and practice it, and having described the presently preferred embodiments thereof, I claim:

1. A process for harvesting a plant compound which is stored in the living epidermal cells of a plant and which absorbs light having a wavelength in the range of 260 to 400 nm, comprising the steps of
   (a) subjecting at least a portion of the living epidermal cells of the plant for a selected period of time to artificial light having a selected illuminance to increase the concentration of the plant compound in the living epidermal cells, the artificial light having at least one wavelength in the range of 260 nm to 400 nm;
   (b) grinding the plant to form a slurry including the epidermal cells from step (a);
   (c) mixing an enzyme in the slurry to produce an enzyme reaction slurry, said enzyme promoting the breaching of the outer walls of the epidermal cells to release the plant compound from the epidermal cells in the slurry;
   (d) adding a solvent to said enzyme reaction slurry to form a solvent-enzyme reaction slurry, said solvent extracting the plant compound from said enzyme reaction slurry; and,
   (e) separating said solvent and the plant compound carried in said solvent from said solvent-enzyme reaction slurry.

2. The process of claim 1, wherein the plant compound is a chalcone.

3. The process of claim 1, wherein the plant compound is a flavanone.

4. The process of claim 1, wherein the plant compound is an anthocyanidin.

5. The process of claim 1, wherein the plant compound is a flavan 3,4-diol.

6. The process of claim 1, wherein the plant compound is an aurone.

7. The process of claim 1, wherein the plant compound is a flavone.

8. The process of claim 1, wherein the plant compound is a flavonol.

9. The process of claim 1, wherein the plant compound is an oligomeric flavonoid.

10. The process of claim 1, wherein the plant compound is a biflavonoid.

11. The process of claim 1, wherein the plant compound is an isoflavonoid.

12. The process of claim 1, including the additional step after step (e) of separating the plant compound from the solvent.

13. The process of claim 1 wherein in step (a) the concentration of the compound in the living epidermal cells is increased by at least one hundred percent.

14. The process of claim 1 wherein in step (a) the concentration of the compound in the living epidermal cells is increased by at least two hundred percent.

15. The process of claim 1 wherein in step (d) said solvent is liquid carbon dioxide.

16. The process of claim 1 wherein in step (d) said solvent is DMSO.

17. The process of claim 1 wherein in step (d) said solvent is ethanol.

18. The process of claim 1 wherein in step (d) said solvent is methanol.

19. The process of claim 1 wherein said illuminance is greater than 3000 lumens per square foot.

20. The process of claim 1 wherein said artificial light has at least one wavelength in the range of 260 to 800 nm.

* * * * *